(12) United States Patent
Ishiwata et al.

(10) Patent No.: US 9,000,110 B2
(45) Date of Patent: Apr. 7, 2015

(54) FLUOROALKYL GROUP-CONTAINING N-SUBSTITUTED (METH)ACRYLAMIDE COMPOUND, POLYMER THEREOF, AND USE THEREOF

(75) Inventors: Fusae Ishiwata, Chigasaki (JP); Ryo Hirabayashi, Chigasaki (JP); Hirotaka Shimizu, Chigasaki (JP)

(73) Assignee: AGC Seimi Chemical Co., Ltd., Chigasaki-shi (JP)

( * ) Notice: Subject to any disclaimer, the term of this patent is extended or adjusted under 35 U.S.C. 154(b) by 369 days.

(21) Appl. No.: 13/391,120

(22) PCT Filed: Aug. 17, 2010

(86) PCT No.: PCT/JP2010/063866
§ 371 (c)(1),
(2), (4) Date: Feb. 17, 2012

(87) PCT Pub. No.: WO2011/021623
PCT Pub. Date: Feb. 24, 2011

(65) Prior Publication Data
US 2012/0149860 A1    Jun. 14, 2012

(30) Foreign Application Priority Data
Aug. 20, 2009 (JP) .................................. 2009-190833

(51) Int. Cl.
C08F 22/38      (2006.01)
C08F 20/58      (2006.01)
C07C 233/49    (2006.01)
C08F 220/22    (2006.01)

(52) U.S. Cl.
CPC .............. C07C 233/49 (2013.01); C08F 20/58 (2013.01); C08F 220/22 (2013.01)

(58) Field of Classification Search
CPC .................................. C08F 22/38; C08F 20/58
USPC ................. 526/242, 245, 246; 548/536, 953; 560/172
See application file for complete search history.

(56) References Cited

U.S. PATENT DOCUMENTS 3,997,604 A * 12/1976 Foulletier et al. ............. 564/204
4,931,582 A    6/1990 Heilmann et al.
4,971,424 A   11/1990 Babirad et al.
4,971,870 A   11/1990 Kato et al.
5,219,705 A    6/1993 Kato et al.
5,368,931 A * 11/1994 Kato et al. .................... 428/327
8,598,291 B2 * 12/2013 Hara et al. .................... 526/245

FOREIGN PATENT DOCUMENTS

| JP | 60 262812 | 12/1985 |
|---|---|---|
| JP | 61 9480 | 1/1986 |
| JP | 61 12777 | 1/1986 |
| JP | 1 139667 | 6/1989 |
| JP | 1 266547 | 10/1989 |
| JP | 2 15278 | 1/1990 |
| JP | 2 188561 | 7/1990 |
| JP | 3 185010 | 8/1991 |
| JP | 3 256310 | 11/1991 |
| JP | 6 93212 | 4/1994 |
| JP | 06124006 A * | 5/1994 |
| JP | 7 18243 | 1/1995 |
| JP | 7 18247 | 1/1995 |
| JP | 8 176496 | 7/1996 |
| JP | 10 158462 | 6/1998 |
| JP | 10 287867 | 10/1998 |
| JP | 2006 169501 | 6/2006 |
| JP | 2008 297482 | 12/2008 |
| WO | 2008 059654 | 5/2008 |
| WO | WO 2008149676 A1 * | 12/2008 |
| WO | 2009 090798 | 7/2009 |

OTHER PUBLICATIONS

International Search Report Issued Sep. 21, 2010 in PCT/JP10/63866 Filed Aug. 17, 2010.
U.S. Appl. No. 14/241,738, filed Feb. 27, 2014, Ishiwata.

* cited by examiner

*Primary Examiner* — Nicole M Buie-Hatcher
(74) *Attorney, Agent, or Firm* — Oblon, McClelland, Maier & Neustadt, L.L.P.

(57) ABSTRACT

A compound represented by the following formula (a):

$$CH_2=CR^1-CONJ-CGR^2-(CH_2)_n-COO-Q^1-Rf^1 \quad (a)$$

is provided. This compound is capable of forming a polymer having an oil repellency equivalent to polymers containing a polyfluoroalkyl group containing at least 8 carbon atoms, although the polyfluoroalkyl group contains up to 6 carbon atoms. In the formula, $R^1$ is hydrogen atom or methyl group, $R^2$ is hydrogen atom or a group represented by $-(CH_2)_m-COO-Q^2-Rf^2$ (r), n and m are independently an integer of 0 to 4, $Rf^1$ and $Rf^2$ are independently a polyfluoroalkyl group or a polyfluoroether group containing 1 to 6 carbon atoms, $Q^1$ and $Q^2$ are independently single bond or a divalent linkage group, J is hydrogen atom or an alkyl group containing 1 to 3 carbon atoms, and G is hydrogen atom or an alkyl group containing 1 to 3 carbon atoms.

18 Claims, No Drawings

FLUOROALKYL GROUP-CONTAINING N-SUBSTITUTED (METH)ACRYLAMIDE COMPOUND, POLYMER THEREOF, AND USE THEREOF

TECHNICAL FIELD

This invention relates to a novel fluoroalkyl group-containing N-substituted (meth)acrylamide compound. This invention also relates to a polymer produced from such compound, a surface treating agent containing such polymer, and an article having a coating containing such polymer.

BACKGROUND ART

Polymers of an acrylate or methacrylate (hereinafter also referred to as "(meth)acrylate") containing a polyfluoroalkyl group are useful for various surface treating agents since they have hydrophobic and lipophobic properties, and they have been used, for example, as a water repellent or oil repellent (see, for example, Patent Literature 1) and as an anti-resin adhesion agent for preventing adhesion of the epoxy resin used as an encapsulating agent of an electronic component to the lead or electrode (see, for example, Patent Literature 2). The fluoroalkyl group used in such surface treating agent has generally been a fluoroalkyl group containing 8 or more carbon atoms, and in particular, a perfluoroalkyl group.

However, biological and environmental accumulativity of perfluorooctanoic acid (PFOA) has recently attracted the attention, and in March 2003, U.S. Environmental Protection Agency (USEPA) published Preliminary Risk Assessment on the safety of the PFOA, and in January, 2006, USEPA advocated participation in the program for reducing environmental emission of PFOA and related chemicals as well as their precursors, and reducing their content in the products to the fluororesin producing companies, and the like. As a consequence, purchase and use of compounds having a perfluoroalkyl group with the chain length of 8 or more have become difficult.

A perfluoroalkyl group exhibits greatly reduced biological and environmental risk when the number of carbon atoms is up to 6. On the other hand, hydrophobic and lipophobic performance is markedly lost, and in particular dynamic hydrophobic and lipophobic performance is lost when the perfluoroalkyl group in the polymer contains up to 6 carbon atoms conceivably because the perfluoroalkyl group containing up to 6 carbon atoms does not form a crystalline structure as in the case of the perfluoroalkyl group containing 8 or more carbon atoms.

CITATION LIST

Patent Literature

Patent Literature 1: JP 10-287867 A
Patent Literature 2: JP 3-256310 A

SUMMARY OF INVENTION

Technical Problems

The present invention has been proposed in view of the situation as described above, and an object of the present invention is to provide a (meth)acrylamide compound having a particular structure capable of forming a polymer having an oil repellency equivalent to that of the polymer containing a polyfluoroalkyl group containing 8 or more carbon atoms although the polyfluoroalkyl group of the polymer is the one containing up to 6 carbon atoms. polymer. Another object of the present invention is to provide a polymer derived from such compound, a surface treating agent containing such polymer, and an article having a coating containing such polymer.

Solution to Problems

The present invention provides a compound represented by the following formula (a).

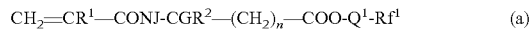

(a)

wherein symbols in the formula are
$R^1$: hydrogen atom or methyl group,
$R^2$: hydrogen atom or a group represented by the following formula (r):

(r)

n and m: independently an integer of 0 to 4,
$Rf^1$ and $Rf^2$: independently a polyfluoroalkyl group or a polyfluoroether group containing 1 to 6 carbon atoms,
$Q^1$ and $Q^2$: independently single bond or a divalent linkage group,
J: hydrogen atom or an alkyl group containing 1 to 3 carbon atoms, and
G: hydrogen atom, an alkyl group containing 1 to 3 carbon atoms, or a group represented by the formula (r)
with the proviso that —CONJ-CGR$^2$- moiety in the formula may be a structure represented by the following formula (s1) or (s2):

[Chemical Formula 1]

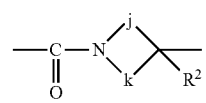

(s1)

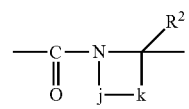

(s2)

j and g: independently single bond or an alkylene group containing 1 to 3 carbon atoms with the proviso that j and g are not simultaneously single bond, and the alkylene group is optionally substituted with the group represented by the formula (r), and
when a two or more groups represented by the formula (r) are present in the compound represented by the formula (a), they may be have the same or different structure.

In the formula (a), both J and G are preferably hydrogen atom. In other words, the compound is preferably the one represented by the following formula (a1):

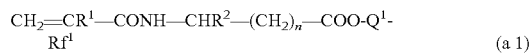

(a1)

wherein symbols in the formula are as defined above.
In the formula (a), the —CONJ-CGR$^2$— in the formula (a) is preferably a structure represented by the formula (s1). In other words, the compound is preferably the one represented by the following formula (a2):

[Chemical Formula 2]

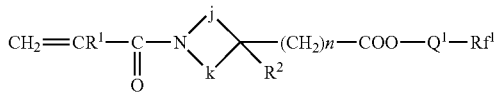
(a2)

wherein symbols in the formula are as defined above.

In the formula (a), formula (a1), or formula (a2), the polyfluoroalkyl group is preferably a perfluoroalkyl group.

In the formula (a), formula (a1), or formula (a2), $Q^1$ and $Q^2$ are preferably a straight chain alkylene group.

The present invention also provides a polymer containing a repeating unit derived from the compound as described above.

The present invention also provides a surface treating agent containing the polymer as described above.

The present invention also provides a surface treating agent which is an anti-resin adhesion agent.

The present invention also provides a surface treating agent which is an anti-flux migration agent.

The present invention also provides an article having a coating containing the polymer as described above.

In the present invention, the article is preferably an electronic component.

Advantageous Effects of Invention

The polymer containing the repeating unit derived from the N-substituted (meth)acrylamide compound of the present invention has reliably realized ecological and environmental safety by using a polyfluoroalkyl group containing up to 6 carbon atoms, and also, maintained the oil repellency equivalent to the polymer containing the repeating unit derived from the conventional compound containing a polyfluoroalkyl group containing at last 8 carbon atoms. In addition, the polymer has also realized anti-resin adhesion performance and IPA repellency in addition to the oil repellency by selecting the structure.

DESCRIPTION OF EMBODIMENTS

The N-substituted (meth)acrylamide compound of the present invention (hereinafter also referred to as the compound of the present invention) is a compound represented by the formula (a). In the present invention, the compound represented by the formula (a) is also referred to as the compound (a), and compounds represented by other formulae are also indicated by the same way. In addition, in the present invention, (meth)acrylamide means both or either one of acrylamide and methacrylamide.

In formula (a), $R^1$ is hydrogen atom or methyl group and $R^1$ may be either one of hydrogen atom and methyl group. For example, $R^1$ is preferably hydrogen atom when the polymer prepared by polymerizing the compound of the present invention is to be provided with a high repellency to n-hexadecane. When the polymer is to be used for an anti-resin adhesion agent, $R^1$ is preferably methyl group.

n is an integer of 0 to 4, and preferably 0 or 1 in view of excellent oil repellency.

In the formula (a), $R^2$ is hydrogen atom or the group represented by the following formula (r):

$$—(CH_2)_m—COO-Q^2-Rf^2 \quad (r)$$

wherein m is an integer of 0 to 4, and preferably 0 or 1 in view of excellent oil repellency, and $Rf^2$ is a polyfluoroalkyl group or polyfluoroether group containing 1 to 6 carbon atoms, and examples are the same as those of $Rf^1$ as described below which is either the same with or different from $Rf^1$.

In view of the excellent anti-resin adhesion performance, $R^2$ is preferably a group represented by the formula (r).

$Q^2$ is single bond or a divalent linkage group, and examples are the same as those of $Q^1$ as described below which is either the same with or different from $Rf^1$.

In formula (a), $Rf^1$ is a polyfluoroalkyl group or a polyfluoroether group containing 1 to 6 carbon atoms.

A polyfluoroalkyl group is a fluoro-substituted or perfluoro-substituted alkyl group wherein two to all hydrogen atoms of the alkyl group have been substituted with fluorine atom. The polyfluoroalkyl group may have a straight chain or branched structure. The number of carbon atoms in the polyfluoroalkyl group is the number including the branch in the case of the branched structure.

Exemplary straight chain structures include methyl group, ethyl group, n-propyl group, n-butyl group, n-pentyl group, and n-hexyl group, and exemplary branched groups include isopropyl group, s-butyl group, t-butyl group, 3-methylbutyl group, isopentyl group, neopentyl group, and isohexyl group.

A polyfluoroether group is a group wherein ethereal oxygen atom has been inserted between carbon atoms of the polyfluoroalkyl group at one or more site.

The number of carbon atoms in the polyfluoroalkyl group is determined so that it includes all carbon atoms to which fluorine atom is bonded, and the number of carbon atoms included in the group would be minimum.

For example, when "-$Q^1$-$Rf^1$" is a group represented by "—$C_2H_4$—$C_6F_{13}$" in the formula (a), $Q^1$ is "$C_2H_4$" and $Rf^1$ is "$C_6F_{13}$", and similarly, when "-$Q^1$-$Rf^1$" is a group represented by "—$CH_2$—$CHF$—$CH_2$—$CF_2H$", $Q^1$ is "$CH_2$" and $Rf^1$ is "$CHF$—$CH_2$—$CF_2H$".

$Rf^1$ and $Rf^2$ in the formula (r) (hereinafter also generally referred to as $R^f$ group) may have a straight chain or branched structure, and in view of improving packing rate of the $R^f$ group, $R^f$ group may preferably have a straight chain structure. For the same reason, when the $R^f$ group has a branched structure, the branched moiety is preferably at the terminal of the $R^f$ group.

$R^f$ group is preferably a polyfluoroalkyl group in view of the excellent oil repellency and anti-resin adhesion performance. Furthermore, $R^f$ group is preferably a fully fluorine-substituted perfluoroalkyl group ($R^F$ group), and more preferably, a straight chain $R^F$ group.

$R^f$ is preferably —$C_6F_{13}$ and —$C_4F_9$ in view of the excellent oil repellency performance and anti-resin adhesion performance.

In the formula (a), $Q^1$ is single bond or a divalent linkage group.

Exemplary divalent linkage groups include a straight chain or branched divalent alkylene group containing 1 to 10 carbon atoms, an alkenylene group containing 2 to 10 carbon atoms, a six-membered cyclic aromatic group, a four to six-membered cyclic saturated or unsaturated alicyclic group, a five to six-membered heterocyclic group, —$(C_2H_4O)_p$—, —$(C_3H_6O)_q$— (wherein p and q are independently 1 to 10 (on average)), or a divalent linkage group represented by the following formula (q). The divalent linkage group may be a combination of such groups, and the cyclic group may be in fused form. Total atomic weight of the divalent linkage group is preferably up to 500.

$$-Y-Z- \quad (q)$$

In the formula, symbols are as defined below.

Y: a straight chain or branched divalent alkylene group containing 1 to 10 carbon atoms, six-membered aromatic group, four to six-membered saturated or unsaturated alicyclic group, five to six-membered heterocyclic group, or a fused ring group thereof, Z: —O—, —S—, —CO—, —COO—, —COS—, —N(R)—, —SO$_2$—, —PO$_2$—, —N(R)—COO—, —N(R)—CO—, —N(R)—SO$_2$—, or —N(R)—PO$_2$—, R: hydrogen atom or an alkyl group containing 1 to 3 carbon atoms, Z may be in reverse direction.

The divalent linkage group may have a substituent, and exemplary substituents include halogen atom (F, Cl, Br, and I), cyano group, alkoxy group (methoxy, ethoxy, butoxy, octyloxy, methoxyethoxy, etc.), aryloxy group (phenoxy, etc.), alkylthio group (methylthio, ethylthio, etc.), acyl group (acetyl, propionyl, benzoyl, etc.), sulfonyl group (methanesulfonyl, benzenesulfonyl, etc.), acyloxy group (acetoxy, benzoyloxy, etc.), sulfonyloxy group (methanesulfonyloxy, toluenesulfonyloxy, etc.), phosphonylgroup (diethylphosphonyl, etc.), amide group (acetylamino, benzoylamino, etc.), carbamoyl group (N,N-dimethylcarbamoyl, N-phenylcarbamoyl, etc.), alkyl group (methyl, ethyl, propyl, isopropyl, cyclopropyl, butyl, etc.), aryl group (phenyl, toluoyl, etc.), heterocyclic group (pyridyl, imidazolyl, furanyl, etc.), alkenyl group (vinyl, 1-propenyl, etc.), alkoxyacyloxy group (acetyloxy, etc.), alkoxycarbonyl group (methoxycarbonyl, ethoxycarbonyl, etc.), and polymerizable group (vinyl group, acryloyl group, methacroyl group, silyl group, cinnamonate residue, etc.).

However, when Q$^1$ and Q$^2$ in the formula (r) are an alkylene group or an oxyalkylene group having the structure substituted with fluorine atom, structure of Q$^1$ and Q$^2$ is determined by the principle of carbon atom number determination of the polyfluoroalkyl group.

Q$^1$ and Q$^2$ are not limited to those as described above, and Q$^1$ and Q$^2$ may be adequately selected as long as they are single bond or a divalent linkage group. However, the preferred are single bond and a straight chain or branched alkylene group, and the most preferred is a straight chain alkylene group.

In the formula (a), J is hydrogen atom or an alkyl group containing 1 to 3 carbon atoms, and G is hydrogen atom, an alkyl group containing 1 to 3 carbon atoms, or a group represented by the formula (r).

However, the —CONJ-CGR$^2$— moiety in the formula may have a structure represented by the following formula (s1) or (s2):

[Chemical Formula 3]

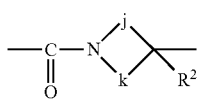

(s1)

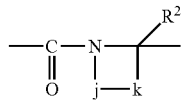

(s2)

wherein j and g are independently single bond or an alkylene group containing 1 to 3 carbon atoms, with the proviso that j and g are not simultaneously single bond. The alkylene group may be substituted with the group represented by the formula (r).

When two or more groups represented by the formula (r) are present in the formula (a), they may be the same or different.

When —CONJ-CGR$^2$— moiety is a structure represented by the formula (s1) or formula (s2), J corresponds to j, and G corresponds to g. However, when J is hydrogen atom, j corresponds to single bond, and when J is an alkyl group, j corresponds to the corresponding alkylene group from which one hydrogen atom has been removed. The relation between G and g is similar. When j or g is single bond in the formula (s1), nitrogen atom and carbon atom in the CR$^2$ would be directly bonded, and when j is single bond in the formula (s2), nitrogen atom and g would be directly bonded. Similarly, when g is single bond in the formula (s2), j and carbon atom in the CR$^2$ would be directly bonded.

Both J and G are preferably hydrogen atom in view of the availability of the starting material as well as excellent oil repellency. Also preferred is the structure wherein —CONJ-CGR$^2$— moiety is the structure represented by the formula (s1).

An exemplary compound (a) of the present invention which is preferable in view of the availability of the starting material as well as excellent oil repellency is the following compound:

$$CH_2=CR^1-CONH-CHR^2-(CH_2)_n-COO-Q^1-Rf^1 \quad (a1)$$

[Chemical Formula 4]

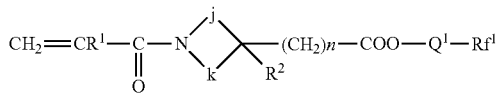

(a2)

wherein symbols in the formula are as defined above.

Of the compounds (a1), the preferred is the following compound (a1-1):

$$CH_2=CR^1-CONH-CHR^2-(CH_2)_n-COO-(CH_2)_p-Rf^1 \quad (a1-1)$$

wherein symbols in the formula are as defined below.

R$^2$: hydrogen atom or the group represented by the following formula (r-1):

$$-(CH_2)_m-COO-(CH_2)_q-Rf^2 \quad (r-1)$$

wherein p and q are an integer of 0 to 6, and n, m, R$^1$, Rf$^1$, and Rf$^2$ are as defined above for the formula (a).

Of the compounds (a1-1), the preferred are the compounds wherein R$^2$ is the group represented by the formula (r-1), namely, the compounds (a1-11):

[Chemical Formula 5]

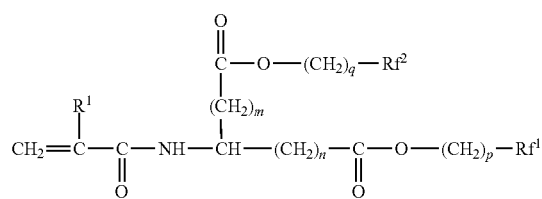
(a-11)

wherein symbols in the formula are as defined above for the formula (a1-1).

Exemplary compounds are the following compounds:

[Chemical Formula 6]

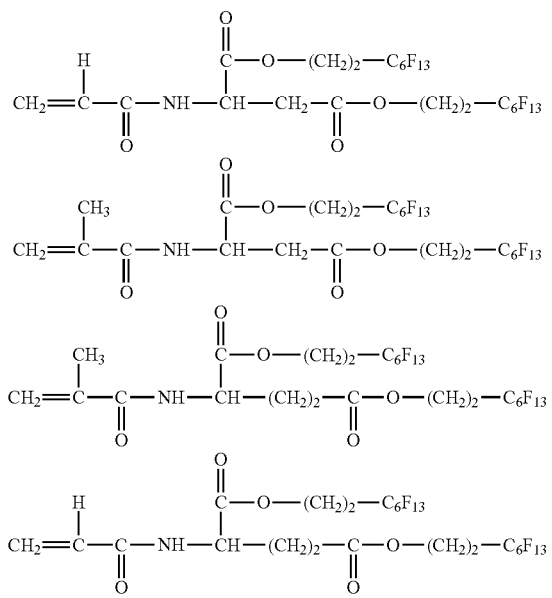

Of the compound (a2), the preferred are the compounds represented by the following compound (a2-1):

[Chemical Formula 7]

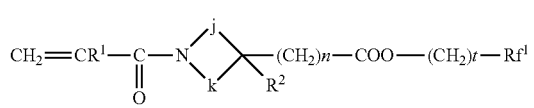
(a2-1)

wherein $R^2$ is hydrogen atom or the group represented by the formula (r-1):

t is an integer of 0 to 6, j, g, n, $R^1$, $Rf^1$, and $Rf^2$ are as defined above for the formula (a).

The compounds wherein j and g are independently an alkylene group containing 1 to 3 carbon atoms include the following compounds:

[Chemical Formula 8]

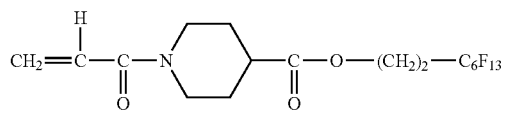

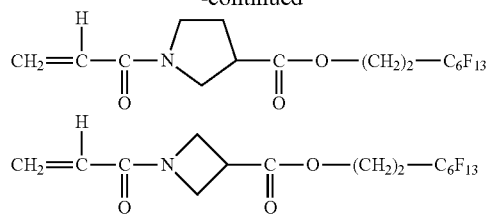

The compounds wherein $R^2$ is hydrogen atom and j is substituted with the group represented by the formula (r) include the following compounds:

[Chemical Formula 9]

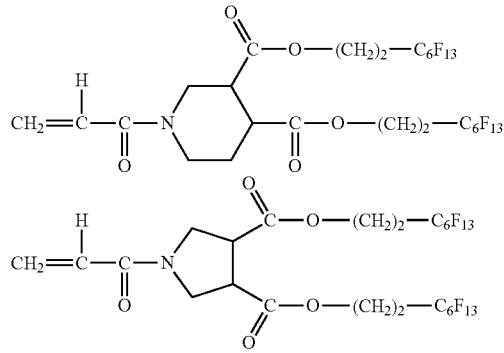

Of the compound (a2-1), compounds wherein j and g are independently an alkylene group containing 1 to 3 carbon atoms are preferable in view of the ease of synthesis, and among those, the most preferred are those wherein both j and g are an alkylene group containing 2 carbon atoms in view of the availability of the starting materials.

The method used for the production of the compound (a) of the present invention is not particularly limited, and the compound (a) may be produced, for example, by a two step method, and more specifically, by a method comprising a first step of esterification of an amino acid and a fluoroalkyl group-containing alcohol to produce the corresponding amino acid ester, and a second step of (meth)acrylamidating the amino acid ester produced in the first step to produce the intended compound (a) of the present invention.

When the procedure is described for the embodiment wherein $R^2$ in the compound (a) is hydrogen atom or —$(CH_2)_m$—COO-$Q^2$-$Rf^2$ which is the same as —$(CH_2)_n$—COO-$Q^1$-$Rf^1$, the procedure will be the one represented by the following scheme.

First step: In this step, the following compound (1) (amino acid) is reacted with the following compound (2) (alcohol) under reflux in the presence of an acid catalyst (3) in a solvent which forms an azeotrope with water. During the reaction, the water generated is removed. The compound (4) (amino acid ester) is thereby produced.

Second step: In this step, the resulting amino acid ester (4) is reacted with a (meth)acrylic acid chloride (5) in the presence of a base to obtain the intended compound (a).

$$NHJ^1—CG^1R^3 (CH_2)_n—COOH \quad (1)$$

wherein $R^3$ is H or —$(CH_2)_n$—COOH $$HO-Q^1-Rf^1 \quad (2)$$

$$X^-H^+ \quad (3)$$

$$X^{-+}NJ^1H_2\text{—}CG^1R^2\text{—}(CH_2)_n\text{—}COO\text{-}Q^1\text{-}Rf^1 \quad (4)$$

$$CH_2\text{=}CR^1\text{—}COCl \quad (5)$$

$$CH_2\text{=}CR^1\text{—}CONJ^1\text{-}CG^1R^2\text{—}(CH_2)_n\text{—}COO\text{-}Q^1\text{-}Rf^1 \quad (a)$$

In the formulae, X is a conjugate base of the acid catalyst (3), and $J^1$ and $G^1$ are independently hydrogen atom or an alkyl group containing 1 to 3 carbon atoms.

However, the —$NJ^1$-$CG^1$- moiety in the formula may be a structure represented by the following formula (s11) or (s21):

[Chemical Formula 10]

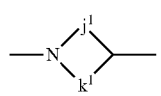
(s11)

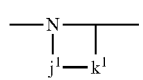
(s21)

wherein $j^1$ and $g^1$ are independently single bond or an alkylene group containing 1 to 3 carbon atoms, with the proviso that $j^1$ and $g^1$ are not simultaneously single bond.

When $R^2$ in the intended compound (a) is —$(CH_2)_m$—COO-$Q^2$-$Rf^2$ which is different from the —$(CH_2)_n$—COO-$Q^1$-$Rf^1$, $R^3$ in the amino acid (1) may be —$(CH_2)_m$—COOH (m ≠ n) and/or the alcohol (2) may be used with another alcohol HO-$Q^2$-$Rf^2$ and the production can be accomplished by the same scheme.

[First Step]

In the first step, various amino acids may be used for the compound (1). Such amino acid is commercially available from Wako Pure Chemical Industries, Ltd., Tokyo Kasei Kogyo Co. Ltd., and the like. Among these, the amino acid is preferably glycine, β-alanine, or aspartic acid when the compound (a1) is to be obtained. When the compound (a2) is to be obtained, the preferred is use of isonipecotic acid.

The alcohol of the compound (2) is commercially available from Wako Pure Chemical Industries, Ltd., Tokyo Kasei Kogyo Co. Ltd., and the like. Alternatively, the alcohol of the compound (2) may be synthesized by a method known in the art (such as those described in JP SH040-1905 B, JP SHO 58-39135 B, JP SHO 52-8807 B, and the like). Examples of the compound (2) include $C_6F_{13}$—$(CH_2)_2$—OH, $C_4F_9$—$(CH_2)_2$—OH, $C_2F_5$—$(CH_2)_2$—OH, and $(CF_3)_2CH$—OH, and the preferred is $C_6F_{13}$—$(CH_2)_2$—OH.

The compound (3) is commercially available from Wako Pure Chemical Industries, Ltd., Tokyo Kasei Kogyo Co. Ltd., and the like. Examples of the compound (3) include p-toluenesulfonic acid, hydrochloric acid, and sulfuric acid, and the preferred is p-toluenesulfonic acid.

The first step is preferably conducted in a solvent.

Preferable solvent is a hydrocarbon solvent which is azeotropic with water.

Examples of such hydrocarbon solvent include hexane, cyclohexane, heptane, benzene, toluene, and xylene, and the preferred is cyclohexane.

The solvent may be used at an amount so that safe and stable reaction is facilitated. Preferably, the solvent is used at 0.2 to 20 times the mass of the compound (1).

The reaction is preferably conducted under reflux while removing the water generated. For the removal of the water generated, the reaction is preferably conducted by using a reaction container equipped with Dean-Stark apparatus or the like.

When $R^3$ is hydrogen atom, the compound (2) is preferably used at 0.7 to 10 equivalents and more preferably at 0.9 to 5 equivalents in relation to the compound (1), and when $R^3$ is "—$(CH_2)_m$—COOH", the compound (2) is preferably used at 1.5 to 20 equivalents, and more preferably at 1.8 to 10 equivalents in relation to the compound (1).

The compound (3) is used at least 1 equivalent in relation to the compound (1). More preferably, compound (3) is used at 1.01 to 3 equivalents in relation to the compound (1).

[Second Step]

In the second step, the compound (5) is commercially available in the form of a reagent from Wako Pure Chemical Industries, Ltd., Tokyo Kasei Kogyo Co. Ltd., and the like. The compound (5) may also be prepared by the acid halide synthesizing method described in the textbook of organic synthesis such as "Lectures on Experimental Chemistry" (Maruzen).

The compound (5) is preferably used at 0.7 to 10 equivalents, and more preferably at 1.0 to 5 equivalents in relation to the compound (4).

The second step is conducted in the presence of a base. Exemplary bases include tertiary amines such as triethylamine and inorganic bases such as sodium carbonate and sodium hydrogencarbonate. Among these, the preferred are tertiary amines such as triethylamine and trimethylamine.

The second step may be conducted by using a solvent.

Various solvents may be used as long as the solvent does not affect the reaction. Exemplary solvents include aprotic polar solvents such as hexane, cyclohexane, benzene, toluene, methylene chloride, chloroform, acetonitrile, acetone, diethylether, DMF, and DMSO and various fluorine solvents. Among these, the preferred are methylene chloride and chloroform in view of the high solubility of the reactants in the solvent.

The solvent may be used at an amount so that safe and stable reaction is facilitated. Preferably, the solvent is used at 0.1 to 20 times the mass of the compound (4).

The reaction is exothermic, and preferably, the compound (4) is gradually added dropwise with the cooling of the reaction container by ice water or the like. When the exothermic phase is completed, the reaction is preferably continued at around room temperature. More specifically, the reaction is preferably conducted at a temperature in the range of 5° C. to 25° C.

The polymer of the present invention is a polymer containing repeating unit (A) derived from the compound (a). The repeating unit (A) derived from the compound (a) may be expressed as:

[Chemical Formula 11]

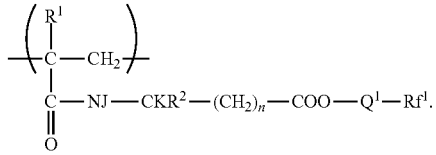

The repeating unit (A) may be the one derived from single type of the compound (a) or a combination of two or more types of the compound (a). In addition, the polymer of the present invention may further contain repeating units other than the repeating unit (A).

In the present invention, when the polymer contains repeating units derived from a plurality of compounds, mass ratio of each repeating unit is the value based on the estimation that all of the starting materials used for the polymerization constitute the repeating unit. Accordingly, mass ratio of the repeating unit (A) (percentage of the mass of the repeating unit (A) in the mass of all repeating units) is calculated substantially as the ratio of the mass of the compound (a) used for the polymerization in relation to total mass of the starting materials for the polymerization. Mass ratio of other repeating units in the polymer is also calculated in the similar way.

In the polymer of the present invention, content of the repeating unit (A) is preferably 5 to 100% by mass, more preferably 10 to 100% by mass, and more preferably 30 to 100% by mass. When the content of the repeating unit (A) in the polymer of the present invention is within such range, the surface treating agent containing the polymer of the present invention will exhibit good oil repelling performance. When the content is 10 to 100% by mass, and more preferably 30 to 100% by mass, the anti-resin adhesion agent containing the polymer of the present invention will exhibit good oil repelling performance, and also, good anti-resin adhesion performance.

In the polymer of the present invention, the repeating unit (A) may comprise either one type or two or more types of the repeating unit (A). When the repeating unit (A) comprises two or more types of such unit, total content of the repeating unit (A) is preferably within the range as described above.

Other repeating units are not particularly limited as long the repeating unit is the one derived from a compound which is copolymerizable with the compound (a). Exemplary such units include repeating unit (B) derived from a fluoro(meth)acrylate having the following structure (compound (b)) and a repeating unit (C) derived from the polymerizable compound (c).

$$CH_2=CR^{b1}-COO-Q^{b1}-Rf^{b1} \quad (b)$$

Symbols in the formula are as defined below.

$R^{b1}$: hydrogen atom or methyl group, $Rf^{b1}$: a polyfluoroalkyl group or polyfluoroether group containing 1 to 6 carbon atoms, $Q^{b1}$: single bond or a divalent linkage group.

In the compound (b), $Rf^{b1}$ may be a group having a structure similar to $Rf^1$ and $Rf^2$ of the compound (a). $Rf^{b1}$ is preferably $-C_6F_{13}$ or $-C_4F_9$ in view of good oil repelling performance and anti-resin adhesion performance.

In the compound (b), the divalent linkage group $Q^{b1}$ may be a group having a structure similar to $Q^1$ and $Q^2$ of the compound (a). $Q^{b1}$ is preferably single bond or a straight chain or branched alkylene group.

In the polymer of the present invention, content of the repeating unit (B) is preferably 0 to 95% by mass, more preferably 0 to 90% by mass, and most preferably 0 to 70% by mass. When the content of the repeating unit (B) in the polymer of the present invention is within such range, the surface treating agent containing the polymer of the present invention will exhibit good oil repelling performance as well as good anti-resin adhesion performance.

In the polymer of the present invention, the repeating unit (B) may comprise either one type or two or more types of the repeating unit (B). When the repeating unit (B) comprises two or more types of such unit, total content of the repeating unit (B) is preferably within the range as described above.

Preferable examples of the compound (b) are:
$CH_2=CH-COO-CH_2-CF_3$,
$CH_2=C(CH_3)-COO-CH_2-CF_3$,
$CH_2=CH-COO-CH_2-CF_2CF_3$,
$CH_2=C(CH_3)-COO-CH_2-CF_2CF_3$,
$CH_2=CH-COO-CH(CF_3)_2$,
$CH_2=C(CH_3)-COO-CH(CF_3)_2$,
$CH_2=CH-COO-(CH_2)_2-(CF_2)_4F$,
$CH_2=C(CH_3)-COO-(CH_2)_2-(CF_2)_4F$,
$CH_2=CH-COO-(CH_2)_2-(CF_2)_6F$,
$CH_2=C(CH_3)-COO-(CH_2)_2-(CF_2)_6F$,
$CH_2=CH-COO-(CH_2)_2-(CF_2)_2CF(CF_3)_2$, and
$CH_2=C(CH_3)-COO-(CH_2)_2-(CF_2)_2CF(CF_3)_2$.

The compound (c) is a compound having a polymerizable group other than the compound (a) or the compound (b). More specifically, the compound (c) may be, for example, a (meth)acrylic acid compound (c1), a styrene compound (c2), or a polymerizable compound (c3) other than (c1) or (c2). Non-limiting examples of such compound (c) are as described below.

Examples of the (c1) include acrylic acid, methacrylic acid, and a (meth)acrylate represented by the following formula:

$$CH_2=C(R^{c1})-COO-Q^{c1}-R^{c2}$$

wherein $R^{c1}$ is hydrogen atom or methyl group, $Q^{c1}$ is single bond or a divalent linkage group, and $R^{c2}$ is $-OH$, $-Si(OAk)_3$ (wherein Ak is a straight chain or branched alkyl group containing 1 to 3 carbon atoms), $-CH_3$, $-CH_2CH_2N(CH_3)_2$, $-(CH_2)_mH$ (m=2 to 20), $-CH_2CH(CH_3)_2$, $-CH_2-C(CH_3)_2-COO-Ph$, $-CH_2Ph$, $-CH_2CH_2OPh$, $-CH_2N^+(CH_3)_3Cl^-$, $-(CH_2CH_2O)_mCH_3$ (m=2 to 20), $-(CH_2)_2-NCO$,

[Chemical Formula 12]

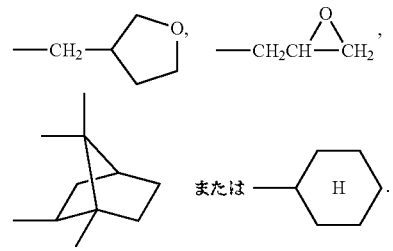

The divalent linkage group $Q^{c1}$ may have a structure similar to the $Q^1$ and $Q^2$ of the compound (a). $Q^{c1}$ is preferably single bond or a straight chain or branched alkylene group.

Other examples of the (c1) include polyester of (meth) acrylic acid such as acrylate diester and compounds represented by the following formula:

$$CH_2=C(R^{c3})-CONR^{c4}-Q^{c2}-R^{c5}$$

wherein $R^{c3}$ is hydrogen atom or methyl group, $R^{c4}$ is $-C_mH_{2m+1}$ (m=2 to 20) or $-H$, $Q^{c2}$ is single bond or a divalent linkage group, $R^{c5}$ is $-H$, $-OH$, $-COOH$, $-CH_3$, $-CH_2CH_2N(CH_3)_2$, $-(CH_2)_mH$ (m=2 to 20), $-CH(CH_3)_2$, $-C(CH_3)_3$, $-C(CH_3)_2SO_3H$, $-CH_2N^+(CH_3)_3Cl$, or -Ph.

Examples of the (c2) include styrene compounds represented the following formula:

[Chemical Formula 13]

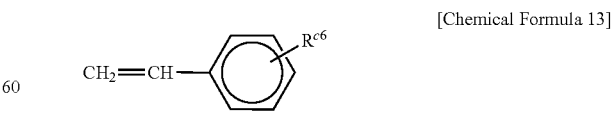

wherein $R^{c6}$ is $-H$, $CH_3$, $-Cl$, $-CHO$, $-COOH$, $-CH_2Cl$, $-CH_2NH_2$, $-CH_2N(CH_3)_2$, $-CH_2N^+(CH_3)_3Cl^-$, $-CH_2N^+H_3Cl^-$, $-CH_2CN$, $-CH_2COOH$, $-CH_2N(CH_2COOH)_2$, $-CH_2SH$, $-CH_2SO_3Na$, or $-CH_2OCOCH_3$.

Other examples of the polymerizable compound (c3) include vinyl compounds other than the (c1) or the (c2), for example, vinyl chloride ($CH_2$=CHCl), and acrylonitrile ($CH_2$=CHCN).

The polymerizable compound (c3) may also be a compound having epoxy group, for example,

[Chemical Formula 14]

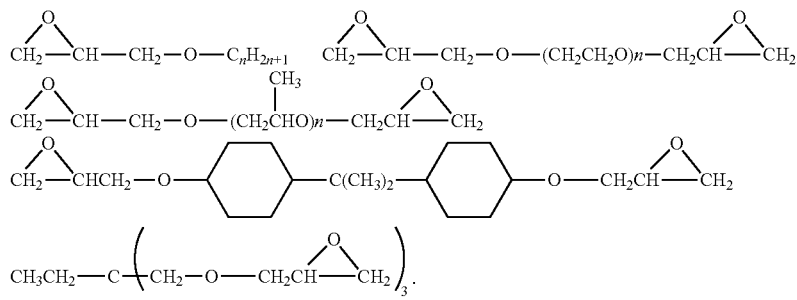

The compound (c) is preferably the following compounds:
$CH_2$=CH—CONH—$CH_2$—$CH_2$—OH,
$CH_2$=C($CH_3$)—CONH—$CH_2$—$CH_2$—OH,
$CH_2$=CH—CONH—$CH_2$—OH,
$CH_2$=C($CH_3$)—CONH—$CH_2$—OH,
$CH_2$=CH—COO—$CH_2$—$CH_2$—OH, and
$CH_2$=C($CH_3$)—COO—$CH_2$—$CH_2$—OH,
in view of improving adhesion to the substrate and realization of the intended effects at low polymer concentration.

In the polymer of the present invention, content of the repeating unit (C) is preferably 0 to 95% by mass, and more preferably 0 to 70% by mass. When the content of the repeating unit (C) in the polymer of the present invention is within such range, the surface treating agent containing the polymer of the present invention will exhibit good oil repelling performance as well as good anti-resin adhesion performance.

In the polymer of the present invention, the repeating unit (C) may comprise either one type or two or more types of the repeating unit (C). When the repeating unit (C) comprises two or more types of such unit, total content of the repeating unit (C) is preferably within the range as described above.

The polymer of the present invention is not particularly limited for its mode of polymerization, and the polymer may be any one of random, block, random, and other polymers.

The polymer of the present invention may be obtained by using various polymerization methods, for example, bulk polymerization, solution polymerization, suspension polymerization, and emulsion polymerization. The source of initiation for the polymerization is not particularly limited, and an initiator commonly used in the art such as an organic peroxide, an azo compound, or a persulphate may be used. In the case of the emulsion polymerization in an aqueous medium, the initiator used may be a water-soluble initiator selected from azo initiators and peroxide initiators.

The polymer of the present invention is not particularly limited for its molecular weight. However, the polymer may preferably have a mass average molecular weight (Mw) of 5000 to 2,000,000, and more preferably 10,000 to 1,500,000. The molecular weight within such range is preferable for realizing satisfactory dynamic oil repellency.

The surface treating agent of the present invention contains the polymer of the present invention. The surface treating agent of the present invention may contain a solvent, and the solvent is not particularly limited as long as the polymer is soluble or dispersible in the solvent. Various solvents may be used and examples include water, hydrocarbon solvents, and fluorine solvents, which may be used alone or in combination of two or more. Of these solvents, the preferred are fluorine solvents including hydrofluorocarbon (HFC) and hydrofluoroether (HFE). Exemplary non-limiting fluorine solvents are as shown below.

m-xylene hexafluoride (hereinafter referred to as m-XHF),
p-xylene hexafluoride,
$CF_3CH_2CF_2CH_3$,
$CF_3CH_2CF_2H$,
$C_6F_{13}OCH_3$,
$C_6F_{13}OC_2H_5$,
$C_3F_7OCH_3$,
$C_3F_7OC_2H_5$,
$C_6F_{13}H$,
$CF_2HCF_2CH_2OCF_2CF_2H$,
$CF_3CFHCFHCF_2CH_3$,
$CF_3(OCF_2CF_2)_n(OCF_2)_mOCF_2H$,
$C_8F_{17}OCH_3$,
$C_7F_{15}OCH_3$,
$C_4F_9OCH_3$,
$C_4F_9OC_2H_5$,
$C_4F_9CH_2CH_3$,
$CF_3CH_2OCF_2CF_2CF_2H$, and
$C_6F_{13}C_2H_5$,
wherein m and n are independently 1 to 20.

The surface treating agent of the present invention is capable of imparting the article treated according to the present invention (treated article) with functions such as oil repellency, antifouling property, lubricity (low friction), non-tackiness, releasability, and surface migration property.

The surface treating agent of the present invention can be used in treating various materials. Exemplary such materials include electric parts (such as electronic circuits and boards and electronic components), frictional parts (such as motor, clock and watch, and HDD), textile products, metal parts (such as mold), stones, filters, and papers. Among these, the preferred is the use for treating electric parts and frictional parts, and in particular, use for electronic components such as capacitor.

Exemplary non-limiting applications of the surface treating agent of the present invention include oil repellent, anti-flux migration agent for solder, oil barrier agent, anti-resin adhesion agent, moisture-proof coating agent, anticorrosive, antifouling agent, and mold release agent. Of these, the compound (a1) is adapted for use as an anti-resin adhesion agent or an anti-flux migration agent for solder, and the compound (a2) is adapted for use as an anti-flux migration agent for solder.

The surface treating agent of the present invention may also contain components other than those as described above as long as such components have no adverse effects on the stability of the composition, oil repellency, outer appearance, and the like. Exemplary such components include pH adjusting agent for preventing corrosion of the coating surface, anticorrosive, dye for the purpose of controlling the concentration of the polymer in the solution when the composition is used after dilution or distinguishing untreated article from the treated article, dye stabilizer, flame retardant, antifoaming agent, and antistatic agent.

The surface treating agent of the present invention may be used at different concentrations suitable for each application. In the case of a water-proof or moisture-proof coating agent, the polymer of the present invention is preferably used at a concentration of 1 to 20% by mass. In the case of an agent for preventing oozing of the lubricating oil or an anti-resin adhesion agent, the polymer of the present invention is preferably used at a concentration of 0.01 to 5% by mass, and in the case of an anti-flux migration agent for solder, the polymer of the present invention is preferably at a concentration of 0.01 to 1% by mass.

Concentration of the polymer of the present invention in the surface treating agent of the present invention may be the final concentration. For example, when an anti-flux migration agent for solder of the present invention is directly prepared, there is no problem if the polymer concentration (concentration of the solid content) in the solution containing the as-polymerized polymer is in excess of 1% by mass. The solution containing the polymer at a high concentration can be diluted so that the solution finally has the preferable concentration as described above, and the resulting diluted solution can be used for the surface treating agent with no further processing.

The article of the present invention has a coating containing the polymer of the present invention at least on a part of the article surface by coating the surface treating agent of the present invention on the article.

The coating is formed by the removal of the solvent from the surface treating agent of the present invention, and the coating mainly comprises the polymer of the present invention. The expression "mainly" means that the coating may solely comprise the polymer of the present invention, or additionally contain other components to the extent not exerting adverse effects.

Content of the polymer of the present invention in the coating is preferably at least 95% by mass, and more preferably at least 99% by mass.

The coating may be accomplished by the coating method commonly used in the art, for example, coating by dipping, spraying, or roller coating.

After the coating of the surface treating agent of the present invention, the coating is preferably dried at a temperature not less than the boiling point of the solvent. Off course, the drying should be accomplished by avoiding the heating if such drying by heating is difficult due to the material of the treated article. The heat treatment conditions may be selected depending on the formulation of the composition coated, area coated by the coating, and the like.

When the surface treating agent of the present invention is an anti-resin adhesion agent, the anti-resin adhesion agent may be coated to a part (for example, lead) of the electronic component to which adhesion of the epoxy resin or the like is to be avoided to thereby form the coating of the anti-resin adhesion agent.

When the surface treating agent of the present invention is an anti-flux migration agent for solder, the anti-flux migration agent may be coated to a part (for example, connecter) of the electronic component to which the flux migration is to be avoided to thereby form the coating of the anti-flux migration agent.

The surface treating agent of the present invention is preferably the one capable of forming a hard coating. When the coating is hard, various effects of the surface treating agent are readily realized, and when the article having the coating formed on its surface is processed, for example, by cutting, the polymer of the present invention is less likely to become attached to the part such as a mold that has been cut. For example, in the case of the anti-flux migration agent, when the part is cut after the formation of the coating, the polymer is less likely to become attached to the cut mold. While the hardness of the coating can be evaluated by various methods, exemplary criteria for the evaluation include high glass transition temperature (Tg) and high melting point (Tm).

EXAMPLES

Next, the present invention is described in detail by referring to the following Examples which by no means limit the scope of the present invention. Unless otherwise noted, "%" in the following Example is "% by mass".

The compounds referred by symbols in the following Examples and Comparative Examples are shown in Table 1.

TABLE 1

| Compound (a-1) | $CH_2=C(CH_3)-CONH-CH_2-COO-(CH_2)_2-C_6F_{13}$ |
| --- | --- |
| Compound (a-2) | $CH_2=CH-CONH-CH_2-COO-(CH_2)_2-C_6F_{13}$ |
| Compound (a-3) | $CH_2=C(CH_3)-CONH-(CH_2)_2-COO-(CH_2)_2-C_6F_{13}$ |
| Compound (a-4) | $CH_2=C(CH_3)-CONH-(CH_2)_3-COO-(CH_2)_2-C_6F_{13}$ |
| Compound (a-5) | $CH_2=C(CH_3)-CONH-(CH_2)_5-COO-(CH_2)_2-C_6F_{13}$ |
| Compound (a-6) | $CH_2=C(CH_3)-C(=O)-NH-CH(CH_2-C(=O)-O-(CH_2)_2-C_6F_{13})-CH_2-C(=O)-O-(CH_2)_2-C_6F_{13}$ |
| Compound (a-7) | $CH_2=C(CH_3)-C(=O)-NH-CH((CH_2)_2-C(=O)-O-(CH_2)_2-C_6F_{13})-CH_2-C(=O)-O-(CH_2)_2-C_6F_{13}$ |
| Compound (a-8) | $CH_2=C(H)-C(=O)-NH-CH(CH_2-C(=O)-O-(CH_2)_2-C_6F_{13})-CH_2-C(=O)-O-(CH_2)_2-C_6F_{13}$ |

TABLE 1-continued

| Compound (a-9) | CH$_2$=C(H)—C(=O)—N(piperidine)—C(=O)—O—(CH$_2$)$_2$—C$_6$F$_{13}$ |
|---|---|
| C6FMA | CH$_2$=C(CH$_3$)—COO—(CH$_2$)$_2$—C$_6$F$_{13}$ |
| C6FA | CH$_2$=CH—COO—(CH$_2$)$_2$—C$_6$F$_{13}$ |
| CmFMA | CH$_2$=C(CH$_3$)—COO—(CH$_2$)$_2$—(CF$_2$)$_n$—F a mixture of compounds wherein n in the formula is 6 to 14, and n on average is 9 |
| HEAA | CH$_2$=CH—CONH—(CH$_2$)$_2$—OH |

Example 1

Synthesis of Compound (a-1)

[First Step]

A 300 ml four neck flask was charged with 21.8 g (60 mmol) of 2-perfluorohexylethyl alcohol, 4.5 g (60 mmol) of glycine (manufactured by Wako Pure Chemical Industries, Ltd.), 11.97 g (63 mmol) of p-toluenesulfonic acid monohydrate (manufactured by Wako Pure Chemical Industries, Ltd.), and 100 g of cyclohexane, and the mixture was refluxed for 17 hours while removing the water generated. The reaction mixture was cooled to 40° C., and subjected to vacuum filtration while washing the precipitated solid with water and acetone. The resulting solid was dried under vacuum, and 27.8 g of glycine 2-perfluorohexylethyl ester p-toluenesulphonate was obtained as a white solid. The yield was 78%.

[Second Step]

A 50 ml flask was charged with a suspension of 5.8 g (10 mmol) of glycine 2-perfluorohexylethyl ester p-toluenesulphonate obtained in the first step in 20 g of methylene chloride, and 2.2 g (22 mmol) of triethylamine (manufactured by Wako Pure Chemical Industries, Ltd.) was added dropwise at 0° C. The mixture was stirred at room temperature for 3 hours, and water was added to cease the reaction. The lower layer of the separated mixture was collected, washed with 1% hydrochloric acid, dried with sodium sulfate, and concentrated under reduced pressure to obtain 3.9 g of the intended compound (a-1) as a pale yellow transparent liquid (purity as measured by gas chromatography, 94%).

$^1$H-NMR and GC-MS data of the resulting compound (a-1) are as described below.

$^1$H-NMR (300 MHz, solvent: CDCl$_3$, standard substance: TMS), σ (ppm): 6.30 (brs, 1H, NHCO), 5.78 (s, 1H, CH$_2$=C), 5.41 (s, 1H, CH$_2$=C), 4.47 (t, 2H, J=6.5 Hz, O—CH$_2$), 4.14-4.10 (m, 2H, N—CH$_2$—COO—CH$_2$), 2.60-2.43 (m, 2H, CH$_2$—CF$_2$), 2.0 (s, 3H, CH$_3$)

GC-MS: M$^+$=489

Example 2

Synthesis of Compound (a-2)

The procedure of Example 1 was repeated by replacing the methacrylic acid chloride with acrylic acid chloride (manufactured by Wako Pure Chemical Industries, Ltd.). Compound (a-2) was synthesized as a white solid.

$^1$H-NMR and GC-MS data of the resulting compound (a-2) are as described below.

$^1$H-NMR (300 MHz, solvent: CDCl$_3$, standard substance: TMS), σ (ppm): 6.34 (dd, 1H, J=17.0, 1.4 Hz, CH$_2$=C), 6.17 (dd, 1H, J=17.1, 10.1, CH$_2$=C), 6.12 (s, 1H, NH), 5.72 (dd, 1H, J=10.2, 1.4 Hz, CH$_2$=CH), 4.49 (t, 2H, J=6.5 Hz, O—CH$_2$), 4.16 (d, 2H, J=5.3 Hz, N—CH$_2$—CO), 2.43-2.60 (m, 2H, CH$_2$—CF$_2$)

GC-MS: M$^+$=475

Example 3

Synthesis of Compound (a-3)

The procedure of Example 1 was repeated by replacing the glycine with β-alanine (manufactured by Wako Pure Chemical Industries, Ltd.). Compound (a-3) was synthesized as a pale yellow transparent liquid.

$^1$H-NMR and GC-MS data of the resulting compound (a-3) are as described below.

$^1$H-NMR (300 MHz, solvent: CDCl$_3$, standard substance: TMS), σ (ppm): 6.39 (brs, 1H, NH) 5.69 (s, 1H, CH$_2$=C), 5.33 (s, 1H, CH$_2$=C), 4.42 (t, 2H, J=6.5 Hz, O—CH$_2$) 3.63-3.51 (m, 2H, N—CH$_2$), 2.62 (t, 2H, J=5.9 Hz, CH$_2$—CO), 2.58-2.43 (m, 2H, CH$_2$—CF$_2$), 1.95 (s, 3H, CH$_3$)

GC-MS: M$^+$=503

Example 4

Synthesis of Compound (a-4)

The procedure of Example 1 was repeated by replacing the glycine with 4-amino butyric acid (Manufactured by Tokyo Kasei Kogyo Co. Ltd.). Compound (a-4) was synthesized as a pale yellow transparent liquid.

$^1$H-NMR and GC-MS data of the resulting compound (a-4) are as described below.

$^1$H-NMR (300 MHz, solvent: CDCl$_3$, standard substance: TMS), σ (ppm): 6.01 (brs, 1H, NH), 5.71 (s, 1H, CH$_2$=C), 5.33 (s, 1H, CH$_2$=C), 4.39 (t, 2H, J=6.5 Hz, O—CH$_2$), 3.40-3.27 (m, 2H, N—CH$_2$), 2.56-2.23 (m, 4H, CH$_2$—CO, CH$_2$—CF$_2$), 1.96-1.83 (m, 5H, CH$_3$, C—CH$_2$—C)

GC-MS: M$^+$=517

Example 5

Synthesis of Compound (a-5)

The procedure of Example 1 was repeated by replacing the glycine with 6-aminohexanoic acid (manufactured by Wako Pure Chemical Industries, Ltd.). Compound (a-5) was synthesized as a white solid.

$^1$H-NMR and GC-MS data of the resulting compound (a-5) are as described below.

$^1$H-NMR (300 MHz, solvent: CDCl$_3$, standard substance: TMS), σ (ppm): 5.98 (brs, 1H, NH), 5.67 (s, 1H, CH$_2$=C), 5.31 (s, 1H, CH$_2$=C), 4.38 (t, 2H, J=6.5 Hz, O—CH$_2$), 3.35-3.28 (m, 2H, N—CH$_2$), 2.56-2.29 (m, 4H, CH$_2$—CO, CH$_2$—CF$_2$), 1.96 (s, 3H, CH$_3$), 1.72-1.52 (m, 4H, —CH$_2$—), 1.32-1.43 (m, 2H, —CH$_2$—)

GC-MS: M$^+$=545

Example 6

Synthesis of Compound (a-6)

The procedure of Example 1 was repeated by replacing the glycine with 4.0 g (30 mmol) of L-aspartic acid (manufactured by Wako Pure Chemical Industries, Ltd.) and the p-toluenesulfonic acid monohydrate was used at an amount of 6.0 g (32 mmol). Compound (a-6) was synthesized as a pale yellow solid.

$^1$H-NMR and GC-MS data of the resulting compound (a-6) are as described below.

$^1$H-NMR (300 MHz, solvent: CDCl$_3$, standard substance: TMS), σ (ppm): 6.80 (d, 1H, J=7.7 Hz, NH), 5.77 (s, 1H, CH$_2$=C), 5.41 (s, 1H, CH$_2$=C), 4.95-4.89 (m, 1H, CH), 4.59-4.32 (m, 4H, 0-CH$_2$), 3.13-2.92 (m, 2H, CH$_2$—CO), 2.57-2.38 (m, 4H, CH$_2$—CF$_2$), 1.97 (s, 3H, CH$_3$)

GC-MS: M$^+$=893

Example 7

Synthesis of Compound (a-7)

The procedure of Example 6 was repeated by replacing the L-aspartic acid with L-glutamic acid (manufactured by Wako Pure Chemical Industries, Ltd.). Compound (a-7) was synthesized as a pale yellow viscous liquid.

$^1$H-NMR and GC-MS data of the resulting compound (a-7) are as described below.

$^1$H-NMR (300 MHz, solvent: CDCl$_3$, standard substance: TMS), σ (ppm): 6.66 (d, 1H, J=7.5 Hz, NH), 5.78 (s, 1H, CH$_2$=C), 5.41 (s, 1H, CH$_2$=C), 4.68 (td, 1H, J=7.8, 5.0 Hz, CH), 4.53-4.37 (m, 4H, O-CH$_2$), 2.60-2.38 (m, 6H, CH$_2$—CF$_2$, CH$_2$—CO), 2.33-2.22 (m, 1H, —CH$_2$—), 2.13-2.01 (m, 1H, —CH$_2$—)

GC-MS: M$^+$=907

Example 8

Synthesis of Compound (a-8)

The procedure of Example 6 was repeated by replacing the methacrylic acid chloride with acrylic acid chloride (manufactured by Wako Pure Chemical Industries, Ltd.). Compound (a-8) was synthesized as a white solid.

$^1$H-NMR and GC-MS data of the resulting compound (a-8) are as described below.

$^1$H-NMR (300 MHz, solvent: CDCl$_3$, standard substance: TMS), σ (ppm): 6.71 (d, 1H, J=7.9 Hz, NH), 6.36-6.12 (m, 2H, CH$_2$=CH), 5.73-5.65 (m, 1H, CH$_2$=C), 4.99-4.95 (m, 1H, CH), 4.59-4.31 (m, 4H, O—CH$_2$), 3.13-2.91 (m, 2H, CH$_2$—CO), 2.57-2.39 (m, 4H, CH$_2$—CF$_2$)

GC-MS: M$^+$=879

Example 9

Synthesis of Compound (a-9)

The procedure of Example 1 was repeated by replacing the glycine with isonipecotic acid (Manufactured by Tokyo Kasei Kogyo Co. Ltd.). Compound (a-9) was synthesized as pale yellow transparent liquid.

$^1$H-NMR and GC-MS data of the resulting compound (a-9) are as described below.

H-NMR (300 MHz, solvent: CDCl$_3$, standard substance: TMS), σ (ppm): 6.62-6.53 (m, 1H, =CH$_2$—CO), 6.30-6.23 (m, 1H, CH$_2$=C), 5.71-5.67 (m, 1H, CH$_2$=C), 4.49-4.40 (m, 3H, O—CH$_2$, N—CH$_2$—), 3.98-3.94 (m, 1H, N—CH$_2$—), 3.21-2.86 (m, 2H, N—CH$_2$—), 2.65-2.40 (m, 3H, CH$_2$—CF$_2$, CH—CO), 2.34-1.62 (m, 4H, —CH$_2$—)

GC-MS: M$^+$=529

Example 10

1 g of compound (a-1) obtained in Example 1, 2 g of m-XHF, and 0.01 g of an initiator V-601 (dimethyl 2,2'-azobis (2-methyl propionate) manufactured by Wako Pure Chemical Industries, Ltd.) were charged in a sealed container, and the mixture was allowed to undergo polymerization at 70° C. for 18 hours. After the reaction, the mixture was purified by precipitation from methanol to obtain polymer (1) as a white solid.

The polymerization was repeated by replacing the compound (a-1) with each of the compounds shown in Table 2 at the mass ratio shown in the table to obtain polymers (2) to (18) as a white solid.

Example 11

2.94 g of the compound (a-2) obtained in Example 2, 0.06 g of HEAA, 12 g of m-XHF, and 0.03 g of an initiator V-601 (dimethyl 2,2'-azobis(2-methyl propionate) manufactured by Wako Pure Chemical Industries, Ltd.) were charged in a sealed container, and the mixture was allowed to undergo polymerization at 70° C. for 18 hours. After the reaction, the mixture was purified by precipitation from methanol to obtain polymer (19) as a white solid.

Example 12

4.98 g of the compound (a-6) obtained in Example 6, 0.02 g of HEAA, 10 g of m-XHF, and 0.03 g of an initiator V-601 (dimethyl 2,2'-azobis(2-methyl propionate manufactured by Wako Pure Chemical Industries, Ltd.) were charged in a sealed container, and the mixture was allowed to undergo polymerization at 70° C. for 18 hours. After the reaction, the mixture was purified by precipitation from methanol to obtain polymer (20) as a white solid.

Example 13

The procedure of Example 12 was repeated except that the polymerization was conducted by replacing compound (a-6) with compound (a-8) to obtain polymer (21) as white solid.

TABLE 2

| Polymer | Monomer mass ratio | | | | | | | | | | | |
|---|---|---|---|---|---|---|---|---|---|---|---|---|
| | Compound (a-1) | Compound (a-2) | Compound (a-3) | Compound (a-4) | Compound (a-5) | Compound (a-6) | Compound (a-7) | Compound (a-8) | Compound (a-9) | C6FMA | C6FA | HEAA |
| (1) | 100 | | | | | | | | | | | |
| (2) | | 100 | | | | | | | | | | |
| (3) | | | 100 | | | | | | | | | |
| (4) | | | | 100 | | | | | | | | |
| (5) | | | | | 100 | | | | | | | |
| (6) | | | | | | 100 | | | | | | |

TABLE 2-continued

| Polymer | Monomer mass ratio | | | | | | | | | | | |
|---|---|---|---|---|---|---|---|---|---|---|---|---|
| | Compound (a-1) | Compound (a-2) | Compound (a-3) | Compound (a-4) | Compound (a-5) | Compound (a-6) | Compound (a-7) | Compound (a-8) | Compound (a-9) | C6FMA | C6FA | HEAA |
| (7) | | | | | | | 100 | | | | | |
| (8) | | | | | | | | 100 | | | | |
| (9) | | | | | | | | | 100 | | | |
| (10) | 80 | | | | | | | | | 20 | | |
| (11) | 50 | | | | | | | | | 50 | | |
| (12) | 30 | | | | | | | | | 70 | | |
| (13) | 80 | | | | | | | | | | 20 | |
| (14) | | | | | | 90 | | | | 10 | | |
| (15) | | | | | | 80 | | | | 20 | | |
| (16) | 50 | | | | | | | | | | 50 | |
| (17) | | | | | | 95 | | | | | 5 | |
| (18) | | | | | | 90 | | | | | 10 | |
| (19) | | 98 | | | | | | | | | | 2 |
| (20) | | | | | | 99.6 | | | | | | 0.4 |
| (21) | | | | | | | | 99.6 | | | | 0.4 |

Comparative Production Example 1

The procedure of Example 8 was repeated except that the polymerization was homopolymerization of C6FMA to obtain comparative polymer (1) as a white solid.

Comparative Production Example 2

The procedure of Example 8 was repeated except that the polymerization was homopolymerization of C6FA to obtain comparative polymer (2) as a white solid.

Comparative Production Example 3

22.5 g of CmFMA, 52.5 g of m-XHF, and 18.8 mg of an initiator AIBN were charged in a sealed container, and the mixture was allowed to undergo polymerization at 70° C. for 15 hours. After the reaction, m-XHF was added, and comparative polymer (3) was obtained as a 17% solution.

In the 2-perfluoroalkylethyl methacrylate having an alkyl group containing 9 carbon atoms on average used in the Comparative Production Example 3, content of the 2-perfluoroalkylethyl methacrylate having an alkyl group containing 6 carbon atoms was 2% (when analyzed by GC).

Example 14

Each of the polymers (1) to (21) obtained in Examples 10 to 13 was diluted with m-XHF to prepare a solution having a concentration of 1%. Surface treating agents (1) to (21) were thereby obtained.

Comparative Examples 1 to 3

The procedure of Example 14 was repeated by using the comparative polymers (1) to (3) produced in Comparative Production Examples 1 to 3 to prepare a solution having a concentration of 1% for use as comparative treating agent (1) to (3).

The resulting surface treating agents (1) to (21) and comparative treating agents (1) to (3) were evaluated for their dynamic contact angle and anti-resin adhesion performance.

[Measurement Procedure of Dynamic Contact Angle]

The surface treating agents (1) to (21) and the comparative treating agents (1) to (3) was adjusted to room temperature, and the glass plate was immersed in the agent. After 1 minute, the glass plate was collected, and dried at about 120° C. for 5 minutes to thereby form the coating.

Next, 20 μl of n-hexadecane (n-HD) or n-butyl glycidyl ether (BGE) was dropped on the glass plate having the coating of the surface treatment agent, and the glass plate was tilted to measure the dynamic contact angle using an automatic contact angle meter OCA-20 manufactured by Data Physics Corporation. The tilting angle of the glass plate when the droplet started sliding downward was "sliding angle", and the angle formed in the fore and the rear of the droplet while sliding downward was "advancing angle" and "receding angle". The evaluation results are shown in Table 3.

The repellency is greater when the advancing angle and the receding angle are greater, and the sliding angle is smaller. "-" in the table means that the angle was immeasurable.

[Evaluation of Anti-Resin Adhesion Performance]

A tin-plated lead having a length of about 5 cm was prepared, and 3 cm or more of each lead was immersed in the surface treating agents (1) to (21) and the comparative treating agents (1) to (3) for 1 minute to form the coating.

Next, the lead was dried at about 120° C. for 10 minutes, and 2 cm of the lead on the side where the coating had been formed was immersed in the well-stirred epoxy resin composition. The lead was raised at a speed of 1 mm/s, and kept in vertical state in a room at about 25° C. The anti-resin adhesion performance was evaluated "C" when no sagging of the epoxy resin composition was observed, and the epoxy resin composition remained adhered to the immersed 2 cm portion. In contrast, the anti-resin adhesion performance was evaluated "A" when the epoxy resin composition fully moved down to the end of the lead, and "B" when the composition moved halfway down but not to the lowest end of the lead. The results are shown in Table 3.

The epoxy resin composition used was a blend of 100 parts by mass of PELCOAT CE-30 (manufactured by Pelnox Limited) as the main component and 10 parts by mass of PELNOX SP-30 (manufactured by Pelnox Limited) as the diluent.

TABLE 3

| | Dynamic contact angle (degrees) | | | | | | Anti-resin |
| --- | --- | --- | --- | --- | --- | --- | --- |
| | n-HD | | | BGE | | | |
| | Advancing angle | Receding angle | Sliding angle | Advancing angle | Receding angle | Sliding angle | adhesion performance |
| Surface treating agent (1) | 70 | 63 | 8 | 58 | 33 | 8 | A |
| Surface treating agent (2) | 72 | 67 | 5 | 69 | 21 | 14 | A |
| Surface treating agent (3) | 69 | 60 | 8 | 57 | 33 | 8 | A |
| Surface treating agent (4) | 74 | 63 | 12 | 67 | 18 | 14 | A |
| Surface treating agent (5) | 79 | 61 | 14 | 63 | 14 | 14 | B |
| Surface treating agent (6) | 71 | 63 | 7 | 61 | 38 | 8 | A |
| Surface treating agent (7) | 71 | 61 | 9 | 66 | 36 | 13 | A |
| Surface treating agent (8) | 75 | 62 | 13 | 68 | 21 | 16 | B |
| Surface treating agent (9) | 70 | 60 | 3 | 63 | 23 | 28 | A |
| Surface treating agent (10) | 71 | 63 | 7 | 60 | 32 | 10 | A |
| Surface treating agent (11) | 73 | 65 | 7 | 61 | 22 | 14 | A |
| Surface treating agent (12) | 70 | 63 | 7 | 81 | 34 | 17 | A |
| Surface treating agent (13) | 72 | 68 | 5 | 65 | 27 | 12 | A |
| Surface treating agent (14) | 72 | 63 | 8 | 63 | 44 | 7 | A |
| Surface treating agent (15) | 71 | 62 | 8 | 67 | 31 | 14 | A |
| Surface treating agent (16) | 73 | 69 | 5 | — | — | >40 | A |
| Surface treating agent (17) | 75 | 64 | 12 | 68 | 38 | 10 | A |
| Surface treating agent (18) | 73 | 63 | 10 | 67 | 37 | 12 | A |
| Surface treating agent (19) | 73 | 68 | 5 | 63 | 17 | 17 | A |
| Surface treating agent (20) | 76 | 61 | 10 | 62 | 41 | 7 | A |
| Surface treating agent (21) | 75 | 66 | 10 | 66 | 21 | 15 | B |
| Comparative treating agent (1) | 70 | 62 | 8 | — | — | >40 | C |
| Comparative treating agent (2) | — | — | >40 | — | — | >40 | C |
| Comparative treating agent (3) | 75 | 69 | 5 | 69 | 59 | 5 | A |

Example 15

The polymers (2), (6), (8), (9), (16) to (21) obtained in Examples 10 to 13 were respectively diluted with the solvent having the composition and concentration shown in the table to prepare surface treating agents (22) to (39).

Comparative Examples 4 to 7

The comparative polymers (1) and (2) produced in Comparative Production Examples 1 and 2 were diluted by the solvent having the composition and concentration shown in Table 4 to prepare comparative treating agents (4) to (7).

The resulting surface treating agents (22) to (39) and comparative treating agents (4) to (7) were measured for their contact angle with IPA to evaluate the IPA repellency. The results are shown in Table 4.

The contact angle was measured by the procedure as described below. The surface treating agent will be a good anti-flux migration agent when the contact angle with IPA is at least 55 degrees, and preferably at least 60 degrees.

[Measurement of Contact Angle]

A glass plate was immersed in each of the surface treating agents (22) to (39) at room temperature for 1 minute, and after collecting the immersed glass plate and drying at room temperature, the coating of the anti-flux migration agent was treated. 2-propanol (IPA) was dropped on the glass plate to measure the contact angle with an automatic contact angle meter OCA-20 manufactured by Data Physics Corporation.

TABLE 4

| | Polymer | Polymer concentration (%) | Solvent composition (%) HFE-7200 | IPA | Contact angle with IPA (degrees) |
|---|---|---|---|---|---|
| Surface treating agent (22) | (2) | 0.1 | 95 | 5 | 61 |
| Surface treating agent (23) | (6) | 0.1 | 100 | 0 | 60 |
| Surface treating agent (24) | (8) | 0.1 | 100 | 0 | 63 |
| Surface treating agent (25) | (9) | 0.1 | 95 | 5 | 63 |
| Surface treating agent (26) | (16) | 0.1 | 95 | 5 | 60 |
| Surface treating agent (27) | (17) | 0.1 | 95 | 5 | 61 |
| Surface treating agent (28) | (18) | 0.1 | 95 | 5 | 60 |
| Surface treating agent (29) | (19) | 0.1 | 95 | 5 | 61 |
| Surface treating agent (30) | (20) | 0.1 | 100 | 0 | 60 |
| Surface treating agent (31) | (21) | 0.1 | 100 | 0 | 64 |
| Surface treating agent (32) | (2) | 0.05 | 95 | 5 | 61 |
| Surface treating agent (33) | (6) | 0.05 | 100 | 0 | 60 |
| Surface treating agent (34) | (8) | 0.05 | 100 | 0 | 63 |
| Surface treating agent (35) | (9) | 0.05 | 95 | 5 | 61 |
| Surface treating agent (36) | (17) | 0.05 | 95 | 5 | 61 |
| Surface treating agent (37) | (19) | 0.05 | 95 | 5 | 62 |
| Surface treating agent (38) | (20) | 0.05 | 100 | 0 | 61 |
| Surface treating agent (39) | (21) | 0.05 | 100 | 0 | 63 |
| Comparative treating agent (4) | Comparative polymer (1) | 0.1 | 100 | 0 | 64 |
| Comparative treating agent (5) | Comparative polymer (2) | 0.1 | 100 | 0 | 36 |
| Comparative treating agent (6) | Comparative polymer (1) | 0.05 | 100 | 0 | 51 |
| Comparative treating agent (7) | Comparative polymer (2) | 0.05 | 100 | 0 | 33 |

The polymers (2), (6), (8), and (9) and comparative polymers (1) to (3) obtained in Example 10 and Comparative Production Examples 1 to 3 were measured for their glass transition temperature (Tg) and melting point (Tm) using a differential scanning calorimeter DSC-50 (manufactured by Shimadzu Corporation) at a temperature elevation rate of 10° C./min. The results are shown in Table 5.

TABLE 5

| Polymer | Tg (° C.) | Tm (° C.) |
|---|---|---|
| (2) | 141 | 174 |
| (6) | 125 | 158 |
| (7) | 120 | 150 |
| (8) | 100 | 142 |
| (9) | 109 | 154 |
| Comparative Polymer (1) | <60 | — |
| Comparative Polymer (2) | <20 | — |
| Comparative Polymer (3) | 24 | 98 |

As described above, the surface treating agent containing the polymer obtained from the compound (a) of the present invention exhibited the dynamic contact angle equivalent to that of the conventional perfluoroalkyl group containing 8 or more carbon atoms. This means that the present invention has enabled to provide an oil repellent having high performance with greatly reduced biological and environmental risks.

The surface treating agent of the present invention also had repellency and anti-resin adhesion performance for BGE (one component in the epoxy resin) equivalent to that of the conventional surface treating agent. This means that the present invention has enabled to provide an anti-resin adhesion agent having high performance with greatly reduced biological and environmental risks.

The surface treating agent of the present invention had high IPA repellency, and in particular, the high IPA repellency was found to be realized even at a low concentration. This means that the present invention has enabled to provide a high performance anti-flux migration agent with reduced risk of contact failure by the coating having a high IPA repellency.

The surface treating agent of the present invention was also confirmed to form a hard coating due to the high Tg and Tm of the polymer obtained from the compound (a) of the present invention. This is a property favorable for a surface treating agent, and when the surface treating agent is used as an anti-flux migration agent and the article having a coating

The invention claimed is:

1. A compound having a formula (a):

$$CH_2=CR^1-CONJ-CGR^2-(CH_2)_n-COO-Q^1-Rf^1 \quad (a)$$

wherein
$R^1$ is a hydrogen atom or a methyl group,
$R^2$ is a group having a formula (r):
$-(CH_2)_m-COO-Q^2-Rf^2$ (r),
n and m are each independently an integer of 0 to 4,
$Rf^1$ and $Rf^2$ are each independently a polyfluoroalkyl group or a polyfluoroether group having 1 to 6 carbon atoms,
$Q^1$ and $Q^2$ are each independently a single bond or a divalent linkage group,
J is a hydrogen atom or an alkyl group having 1 to 3 carbon atoms, and
G is a hydrogen atom, an alkyl group having 1 to 3 carbon atoms, or a group having the formula (r),
wherein the $-CONJ-CGR^2-$ moiety in formula (a) may be a structure having a formula (s1) or (s2):

(s1)

$$-\underset{O}{\overset{\|}{C}}-N\underset{k}{\overset{j}{\diagup}}\!\!\diagdown\!\!\underset{R^2}{}$$

(s2)

$$-\underset{O}{\overset{\|}{C}}-N\underset{j-k}{\overset{R^2}{|}}$$

wherein j and g are each independently a single bond or an alkylene group containing 1 to 3 carbon atoms wherein j and g are not both a single bond, and the alkylene group is optionally substituted with the group having the formula (r), and when a plurality of groups having the formula (r) are present in the compound having the formula (a), they may have the same structure or different structures.

2. The compound according to claim 1 wherein $Rf^1$ and $Rf^2$ are each a perfluoroalkyl group.

3. The compound of claim 2, wherein $Rf^1$ and $Rf^2$ are each independently selected from the group consisting of $-C_4F_9$ and $-C_6F_{13}$.

4. The compound according to claim 1 wherein $Q^1$ and $Q^2$ are each a straight chain alkylene group.

5. A polymer comprising a repeating unit derived from the compound of claim 1.

6. A surface treating agent comprising the polymer of claim 5.

7. The surface treating agent according to claim 6 wherein the agent is an anti-resin adhesion agent.

8. The surface treating agent according to claim 6 wherein the agent is an anti-flux migration agent.

9. An article wherein the article is at least partly coated by a film comprising the polymer of claim 5.

10. The article according to claim 9 wherein the article is an electronic part.

11. The compound of claim 1, wherein $R^1$ is a hydrogen atom.

12. The compound of claim 1, wherein $R^1$ is a methyl group.

13. The compound of claim 1, wherein $R^2$ is a group having the formula (r), wherein m is 0 or 1.

14. The compound of claim 1, wherein n is 0 or 1.

15. The compound of claim 1, wherein the compound has a formula (a1-11):

(a1-11)

$$CH_2=\underset{R^1}{\overset{|}{C}}-\underset{\underset{O}{\|}}{C}-NH-\underset{(CH_2)_m}{\overset{|}{CH}}-(CH_2)_n-\underset{\underset{O}{\|}}{C}-O-(CH_2)_p-Rf^1$$

with $(CH_2)_m$ bearing $-\underset{\underset{O}{\|}}{C}-O-(CH_2)_q-Rf^2$

16. The compound of claim 1, wherein the compound has a formula selected from the group consisting of (i) to (ix):

(i)

$$CH_2=\underset{H}{\overset{|}{C}}-\underset{\underset{O}{\|}}{C}-NH-\underset{CH_2-\underset{\underset{O}{\|}}{C}-O-(CH_2)_2-C_6F_{13}}{\overset{|}{CH}}-CH_2-\underset{\underset{O}{\|}}{C}-O-(CH_2)_2-C_6F_{13}$$

(ii)

$$CH_2=\underset{CH_3}{\overset{|}{C}}-\underset{\underset{O}{\|}}{C}-NH-\underset{CH_2-\underset{\underset{O}{\|}}{C}-O-(CH_2)_2-C_6F_{13}}{\overset{|}{CH}}-CH_2-\underset{\underset{O}{\|}}{C}-O-(CH_2)_2-C_6F_{13}$$

(iii)

$$CH_2=\underset{CH_3}{\overset{|}{C}}-\underset{\underset{O}{\|}}{C}-NH-\underset{(CH_2)_2-\underset{\underset{O}{\|}}{C}-O-(CH_2)_2-C_6F_{13}}{\overset{|}{CH}}-(CH_2)_2-\underset{\underset{O}{\|}}{C}-O-(CH_2)_2-C_6F_{13}$$

(iv)

$$CH_2=\underset{H}{\overset{|}{C}}-\underset{\underset{O}{\|}}{C}-NH-\underset{(CH_2)_2-\underset{\underset{O}{\|}}{C}-O-(CH_2)_2-C_6F_{13}}{\overset{|}{CH}}-(CH_2)_2-\underset{\underset{O}{\|}}{C}-O-(CH_2)_2-C_6F_{13}$$

(viii)

$$CH_2=\underset{H}{\overset{|}{C}}-\underset{\underset{O}{\|}}{C}-N\text{(piperidine ring with two }-C(=O)-O-(CH_2)_2-C_6F_{13}\text{ substituents)}$$

-continued

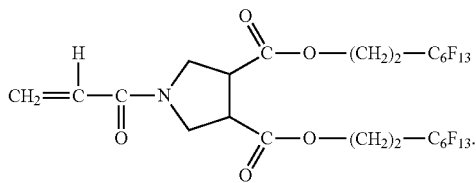

(ix)

17. A compound having a formula (a2):

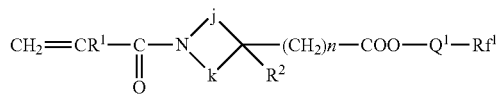

(a2)

wherein
R$^1$ is a hydrogen atom or a methyl group,
R$^2$ is a hydrogen atom or a group having a formula (r):
—(CH$_2$)$_m$—COO-Q$^2$-Rf$^2$ (r),
n and m are each independently an integer of 0 to 4,
Rf$^1$ and Rf$^2$ are each independently a polyfluoroalkyl group or a polyfluoroether group having 1 to 6 carbon atoms,
Q$^1$ and Q$^2$ are each independently a single bond or a divalent linkage group,
j and g are each independently a single bond or an alkylene group having 1 to 3 carbon atoms wherein j and g are not both a single bond,
the alkylene group is optionally substituted with the group having the formula (r), and
when a plurality of groups having the formula (r) are present in the compound having the formula (a), they may have the same structure or different structures.

18. The compound of claim 17, wherein the compound has a formula (a2-1):

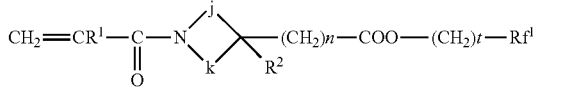

(a2-1)

wherein t is an integer of 0 to 6.

* * * * *